United States Patent
Mentak et al.

(10) Patent No.: US 7,789,509 B2
(45) Date of Patent: Sep. 7, 2010

(54) NON- OR REDUCED GLISTENINGS INTRAOCULAR LENS AND METHOD OF MANUFACTURING SAME

(75) Inventors: Khalid Mentak, San Ramon, CA (US); Margaret Aldred, Ventura, CA (US)

(73) Assignee: Advanced Vision Science, Inc., Goleta, CA (US)

( * ) Notice: Subject to any disclaimer, the term of this patent is extended or adjusted under 35 U.S.C. 154(b) by 505 days.

(21) Appl. No.: 11/804,999

(22) Filed: May 21, 2007

(65) Prior Publication Data

US 2007/0282057 A1 Dec. 6, 2007

Related U.S. Application Data

(60) Provisional application No. 60/810,303, filed on Jun. 1, 2006.

(51) Int. Cl.
*G02C 7/02* (2006.01)
(52) U.S. Cl. .................. 351/177; 264/1.1; 623/6.11
(58) Field of Classification Search ............. 351/177; 623/6.11–6.64; 264/1.1
See application file for complete search history.

(56) References Cited

U.S. PATENT DOCUMENTS

| 4,731,079 A | 3/1988 | Stoy |
| 6,326,448 B1 | 12/2001 | Ojio et al. |
| 2003/0100697 A1* | 5/2003 | Salamone et al. ............. 528/25 |
| 2003/0105255 A1* | 6/2003 | Salamone et al. ........ 526/303.1 |

FOREIGN PATENT DOCUMENTS

| EP | 0 898 972 | 3/1999 |
| WO | WO 96/40303 | 12/1996 |
| WO | WO 2005/047349 | 5/2005 |

OTHER PUBLICATIONS

International Search Report for PCT/US2007/011432 filed May 11, 2007, mailed Dec. 14, 2007, 15 pgs.

* cited by examiner

*Primary Examiner*—Joseph Martinez
*Assistant Examiner*—James R Greece
(74) *Attorney, Agent, or Firm*—Squire, Sanders & Dempsey L.L.P.

(57) ABSTRACT

The present invention relates to an intraocular lens which exhibits reduced or eliminated glistenings when implanted into the eye of a patient in need thereof and to a method of preparing such lens.

12 Claims, No Drawings

NON- OR REDUCED GLISTENINGS INTRAOCULAR LENS AND METHOD OF MANUFACTURING SAME

RELATED APPLICATIONS

This application is related to and claims the benefit of Provisional Patent Application Ser. No. 60/810,303, filed 1 Jun. 2006.

FIELD

This invention relates to the fields of polymer chemistry, materials science and ophthalmology. More particularly it relates to an intraocular lens and method of preparing same that exhibits reduced or no glistenings when implanted in a patient's eye.

BACKGROUND

The following is provided as background solely for the benefit of the reader and is not intended, nor is it to be construed, as prior art to the present invention.

The intraocular lens, which can be surgically implanted in the eye of a patient, has experienced a remarkable history of innovation, each predicated on perceived shortcomings of its predecessor. For instance, the first rigid polymethylmethacrylate (PMMA) lens implanted in the posterior chamber between the iris and the lens by Harold Ridley in 1950 resulted in some relatively serious complications such as decentration or delocalization of the lens due to its size and weight and the frequent occurrence of uveitis. In 1953, a few short years after the introduction of the Ridley lens, anterior chamber, the space between the cornea and the iris, implantable lenses were brought to market. These were held in place in the anterior chamber by a closed loop, which, as the name suggests, comprised a string-like piece of non-optic polymeric material attached at both ends to the lens proper, thus forming a loop. The early closed loops, like the lens itself, were rigid. Unfortunately, these lenses, due to their instability in the anterior capsule, were as prone to complications as the Ridley lens with bullous keratopathy, cystoid macular edema and glaucoma being the more common complications observed. To correct the instability problem, anterior chamber lenses were developed that relied on the papillary portion of the iris for anatomical fixation. Some lens designs required suturing to the iris, some clipped on. This, however, was found to lead to luxation of the lens when the pupil dilated unexpectedly. In about 1970, the anterior lens was again restructured, this time using a flexible closed-loop construct. Corneal damage, however, continued to be a problem and corneal transplants due to implant-related damage to the cornea were not uncommon. The next innovation in intraocular lens was the flexible open loop anterior chamber lens. As suggested by the name, "open loop" refers to a non-optic peripheral appendage that is attached to the lens proper at only one point, the other end of the loop being free to move about and conform to the surface of the eye. This resolved for the most part the corneal problems associated with intraocular lenses but other complications such as cystoid macular oedema continued to occur.

In about 1975, the posterior chamber lens was introduced. As mentioned previously, the posterior chamber is the space behind the iris and in front of the eye's natural lens. While the optic portion of this lens, like its predecessors, was made of PMMA, its haptics, that is, the non-optic portion of the lens at the periphery used to hold the lens in place as exemplified by the closed and open loop configurations, were often made of such materials as polyamide or polypropylene. While these lenses offered numerous advantages such as fewer corneal problems, less retinal detachment and less uveitis-glaucoma-hyphaema (UGH) syndrome, they still required relatively large incisions, approaching 6 mm in length, for implantation. Driven by the advent of phacoemulsion technology for the removal of lenses clouded by cataracts through very small incisions in the eye, foldable intraocular lenses were developed. These lenses can be folded to fit through the same incision used to remove the natural lens, i.e., as small as 2.5-3.0 mm, and then unfolded to operational size once within the eye. One of the predominant types of foldable intraocular lenses presently in use is the so-called hydrophobic acrylic lens as exemplified by the Alcon Acrysof® lens. These lenses, while relatively new in ophthalmology, seem to be avoiding many, if not most, of the complications of their predecessors.

A problem has arisen with the hydrophobic acrylic lenses, however. The lenses, when implanted in a patient's eye, tend over time to form small, light reflective regions in their structure called "glistenings." While the actual cause of glistenings remains unresolved, one theory is that even though these lenses are nominally hydrophobic, over time some water is able to enter into vacuoles in the polymeric matrix comprising the lens thereby changing the refractive index of the lens at those points, which change appears as reflective spots or "glistenings." While there is still some debate over the effect of glistenings at the clinical level, there remains a concern that in worse case scenarios a loss of visual acuity might occur that may require excision of the lens. Even at lesser levels, glistenings can cause glare and other annoyances to patients who have had a hydrophobic intraocular lens implanted.

Thus, there is a need for an acrylic foldable intraocular lens that either is not susceptible to glistenings at all or has a substantially reduced tendency to form glistenings. The present invention provides such a lens.

SUMMARY

Thus, in one aspect, the current invention relates to an intraocular lens comprising an optical polymer or polymer blend having an equilibrium water content of from about 1 wt % to about 12 wt % and sufficient isotonic saline to bring the polymer or polymer blend once it has been formed into a lens to its equilibrium water content at a temperature at or above body temperature, that is, at or above approximately 37° C.

In an aspect of this invention, the intraocular lens is a foldable intraocular lens.

In an aspect of this invention the equilibrium water content of the polymer or polymer blend is from about 2 wt % to about 8 wt %.

In an aspect of this invention, the equilibrium water content of the polymer or polymer blend is from about 3 wt % to about 6 wt %.

In an aspect of this invention the polymer is a copolymer of poly(ethylene glycol)phenyl ether acrylate, styrene, 2-hydroxyethyl methacrylate and ethylene glycol dimethacrylate.

In an aspect of this invention the polymer comprises about 40 wt % poly(ethylene glycol)phenyl ether acrylate, about 26 wt % styrene, about 30 wt % 2-hydroxyethyl methacrylate and about 4 wt % ethylene glycol dimethylacrylate.

In an aspect of this invention, the isotonic saline is selected from the group consisting of balanced salt solution, blood bank saline and phosphate buffered saline.

An aspect of this invention is a method of reducing or eliminating glistenings in an intraocular lens comprising providing an intraocular lens comprising a polymer or polymer blend having an equilibrium water content of from about 1 wt % to about 12 wt % at about 37° C., contacting the intraocular lens with isotonic saline solution at a temperature of about 20° C. to about 90° C. for from about 1 hour to about 36 hours, sterilizing the intraocular lens while maintaining it at its equilibrium water content and implanting the intraocular lens into the eye of a patient in need thereof or storing the intraocular lens in sterile isotonic saline until needed.

An aspect of this invention is the above method wherein the temperature is from about 30° C. to about 80° C. and the time is from about 4 hours to about 30 hours.

An aspect of this invention is the above method wherein the temperature is from about 40° C. to about 70° C. and the time is from about 5 hours to about 24 hours.

An aspect of this invention is the above method wherein the intraocular lens is a foldable intraocular lens.

An aspect of this invention is the above method wherein the intraocular lens is contacted with the isotonic saline solution during manufacture subsequent to solvent extraction and prior to sterilization.

An aspect of this invention is the above method wherein the intraocular lens is contacted with the isotonic saline solution subsequent to sterilization, either during manufacture or after manufacture using sterile isotonic saline solution.

An aspect of this invention is the above method wherein, when the lens is contacted with isotonic saline after manufacture, it has been dried prior to contact with the isotonic saline solution.

An aspect of this invention is the above method wherein the intraocular lens has been commercially packaged prior to contact with the isotonic saline solution.

An aspect of this invention is the above method wherein the equilibrium water content of the polymer or blend of polymers is from about 2 wt % to about 8 wt %.

An aspect of this invention is the above method wherein the equilibrium water content of the polymer or blend of polymers is from about 3 wt % to about 6 wt %.

An aspect of this invention is the above method wherein the polymer is a copolymer comprising poly(ethylene glycol) phenyl ether acrylate, styrene, 2-hydroxyethyl methacrylate and ethylene glycol dimethacrylate.

An aspect of this invention is the above method wherein the polymer comprises about 40 wt % poly(ethylene glycol)phenyl ether acrylate, about 26 wt % styrene, about 30 wt % 2-hydroxyethyl methacrylate and about 4 wt % ethylene glycol dimethylacrylate.

An aspect of this invention is the above method wherein the isotonic saline is selected from the group consisting of balanced salt solution, blood bank saline and phosphate buffered saline.

DETAILED DESCRIPTION

As used herein, an "intraocular lens" refers to a polymeric phakic or aphakic (also referred to in the art as pseudophakic), vision-correcting device that may be implanted into a patient's eye. Phakic lenses are used to correct refractive errors such as myopia (near-sightedness), hyperopia (far-sightedness) and astigmatism (blurred vision due to poor light focusing on the retina due to an irregularly shaped cornea or, in some instances, an irregularly shaped natural lens). The natural lens remains in place when a phakic lens is implanted while the lens is removed prior to implantation of pseudophakic lens. An aphakic or pseudophakic lens is inserted in the eye subsequent to removal of the natural lens due to disease, most often a cataract; that is, clouding of the natural lens. Either type of lens may be implanted in the anterior chamber in front of the iris or in the posterior chamber behind the iris and in front of the natural lens or in the region where the natural lens was before removal. While intraocular lenses may be "hard," that is relatively inflexible, or "soft," i.e., relatively flexible but not foldable, for the purpose of this invention the presently preferred lens is a foldable acrylic polymer lens. A foldable lens is one that is sufficiently flexible that it can be folded into a smaller configuration to permit its implantation into the eye through a much smaller incision that is necessary for hard or soft lenses. That is, while hard and soft lenses may require a 6 mm or larger incision, a foldable lens usually requires only a 3 mm or even smaller incision.

As used herein, the terms "approximately, "essentially," "substantially," "about," "slightly" or any other term of approximation, unless otherwise expressly stated, mean ±5% from the figure set forth.

As used herein, to "contact" a lens with isotonic saline solution refers preferably to submersing the lens in the solution although it is possible to achieve the same result by merely floating the lens atop the isotonic saline solution. As used herein, a "patient" refers to any sighted species suffering from a disorder related to visual acuity. In particular, a patient is a mammal, most particularly a human being. As used herein, a patient is "in need of" an intraocular lens when the patient's natural lens either passes light only partially or not at all as the result of opacification of the lens, or passes light but does not properly focus it on the retina. Such may occur as the result of natural conditions, i.e., aging, or it may occur as a symptom of another disease such as, without limitation, diabetes.

As used herein, a "polymer" refers to a homopolymer prepared by the polymerization of a single monomer or to a copolymer prepared by the polymerization of two or more different monomers. Copolymers may be random, alternating, ordered block, random block or graft copolymers. To be useful in the method of this invention, however, the polymer or copolymer must have an equilibrium water content at approximately body temperature, i.e., about 37° C., from about 1 wt % to about 12 wt %, preferably from about 2 wt % to about 8 wt % and presently most preferably from about 3 wt % to about 6 wt %. Such polymers are generally referred to by those of ordinary skill in the intraocular lens art as "hydrophobic polymers," even though they are capable of absorbing and retaining significant amounts of water.

As used herein, "optical polymer" refers to a polymer that is suitable for implantation into a patient's eye and that is capable of addressing ophthalmic conditions of the lens of the eye such as, without limitation, myopia, hyperopia, astigmatism and cataracts. In general such a polymer will be biocompatible, i.e., will not cause any inflammatory, immunogenic, or toxic condition when implanted will form a clear, transparent, colorless (unless intentionally colored for a particular application) film-like membrane and will have a refractive index greater than about 1.4, preferably greater than about 1.5 and presently most preferably greater than about 1.55.

An example of a presently preferred polymer for use in the intraocular lens and method of this invention is a copolymer of poly(ethylene glycol)phenyl ether acrylate, styrene, 2-hydroxyethyl methacrylate and ethylene glycol dimethacrylate (as a cross-linker). In an embodiment of this invention, the monomers are present in the finished polymer at approximately 40 wt %, 26 wt %, 30 wt % and 4 wt %, respectively. This polymer has an equilibrium water content at about 37° C. (body temperature) of approximately 4%.

As used herein "equilibrium water content" refers to the quantity of isotonic saline solution that a polymer, copolymer or blend of polymers and/or copolymers can absorb at a given temperature, stated as a weight percent (wt %) calculated using the formula EWC (%)=100×($M_h$−$M_d$)/$M_d$, wherein $M_d$ is the weight of the dry polymer and $M_h$ is the weight of the hydrated polymer. For the purposes of this invention, the equilibrium water content is the amount of water that a polymer can contain at about body temperature, that is, about 37° C. To achieve the desired equilibrium water content for a polymer of this invention, the polymer is placed in contact with isotonic saline at about 20° C. to about 90° C. for from about 1 to about 36 hours, preferably at about 30° C. to about 80° C. for from about 4 hours to about 30 hours and presently most preferably at about 40° C. to about 70° C. for from about 5 to about 24 hours.

As used herein, "isotonic saline" refers to a salt, normally sodium chloride, dissolved in water, the amount of salt being substantially the same as that in bodily fluids. For use in the eye, this is approximately 0.8-0.9% w/v (weight per unit volume) of sodium chloride in water. In the metric system, w/v is the same as w/w since a unit volume of water, that is one cubic centimeter, weight one gram. The isotonic saline may be buffered to match intraocular pH by the addition of boric acid and sodium borate or sodium phosphate and potassium phosphate (phosphate-buffered saline, PBS). Presently preferred isotonic saline solutions for use in the intraocular lens and method of this invention are phosphate-buffered saline, such as, without limitation, Dulbecco's buffered phosphate solution; balanced salt solutions such as, again without limitation, Hank's balanced salt solution and Earle's balanced salt solution; and blood bank saline, an approximately 0.85 to 0.9% sodium chloride solution buffered to blood pH (7.0-7.2). Numerous other physiological (i.e., isotonic) saline preparations containing a variety of additional substances are known in the art; any of them that are known or shown to be usable in the eye may be used as the isotonic solution of this invention and all such physiological saline solutions are within the scope of this invention.

An intraocular lens of this invention may be produced as a step in the manufacturing process used to create the lens. For example, without limitation, a manufacturing process may include the steps of polymer synthesis, polymer sheet casting, button cutting, optic lathe cutting, optic milling, haptic attachment, polishing, solvent extraction, sterilization and packaging. The hydration of the lens to equilibrium water content step is currently most preferably, though not necessarily, performed between solvent extraction and sterilization. Hydration to equilibrium water content is accomplished by placing the lens in isotonic saline and heating to from about 20° C. to about 90° C. for from about 1 to about 36 hours, preferably at about 30° C. to about 80° C. for from about 4 hours to about 30 hours and presently most preferably at about 40° C. to about 70° C. for from about 5 to about 24 hours.

It is possible, and it is an embodiment of this invention, to hydrate the lens after sterilization just prior to packaging by using a sterile isotonic saline solution and the above conditions.

It is also possible, and is likewise an embodiment of this invention, to hydrate an intraocular lens of this invention just prior to use. That is, the intraocular lens, current commercial versions of which are normally packaged in the dry state, is removed from its sterile packaging under sterile conditions, placed in sterile isotonic saline and subjected to the above conditions prior to insertion into a patient's eye. If the lens is packaged wet, that is, is already in a sterile isotonic solution, the entire container may be heated to the requisite temperature for the indicated period of time to achieve equilibrium water content prior to implantation in a patient's eye.

As used herein a "commercially packaged" intraocular lens refers to a lens that has been dried and placed in a sterile package for storage until needed. The dry sterile package may be any presently known in the art or as such may become known in the future.

What is claimed:

1. A method of reducing or eliminating glistenings in an intraocular lens, comprising:
    providing an intraocular lens comprising a polymer or polymer blend having an equilibrium water content of from about 1 wt % to about 12 wt % at about 37° C.;
    contacting the intraocular lens with isotonic saline solution at a temperature of about 20 ° C. to about 90 ° C. for from about 1 hour to about 36 hours;
    sterilizing the intraocular lens while maintaining it at its equilibrium water content; and,
    implanting the intraocular lens into the eye of a patient in need thereof or storing the intraocular lens in sterile isotonic saline until needed for implantation into the eye of a patient in need thereof, wherein:
    the polymer or polymer blend comprises a copolymer of poly(ethylene glycol) phenyl ether acrylate, styrene, 2-hydroxyethyl methacrylate and ethylene glycol dimethacrylate.

2. The method of claim 1, wherein the temperature of the isotonic saline solution is from about 30 ° C. to about 80 ° C. and the contact time is from about 4hours to about 30 hours.

3. The method of claim 1, wherein the temperature of the isotonic saline solution is from about 40 ° C. to about 70 ° C. and the contact time is from about 5hours to about 24 hours.

4. The method of claim 1, wherein the intraocular lens is foldable.

5. The method of claim 1, wherein the intraocular lens is contacted with the isotonic saline solution during manufacture subsequent to solvent extraction and prior to sterilization.

6. The method of claim 1, wherein the intraocular lens is contacted with the isotonic saline solution subsequent to sterilization, either during manufacture or after manufacture using sterile isotonic saline solution.

7. The method of claim 6, wherein when the lens is contacted with isotonic saline after manufacture, it has been dried prior to contact with the isotonic saline solution.

8. The method of claim 1, wherein the intraocular lens has been commercially packaged prior to contact with the isotonic saline solution.

9. The method of claim 1, wherein the equilibrium water content of the polymer or blend of polymers is from about 2 wt % to about 8 wt % at about 37 ° C.

10. The method of claim 1, wherein the equilibrium water content of the polymer or blend of polymers is from about 3 wt % to about 6 wt % at about 37 ° C.

11. The method of claim 1, wherein the polymer comprises about 40 wt % poly(ethylene glycol) phenyl ether acrylate, about 26 wt % styrene, about 30 wt % 2-hydroxyethyl methacrylate and about 4 wt % ethylene glycol dimethylacrylate.

12. The method of claim 1, wherein the isotonic saline is selected from the group consisting of balanced salt solution, blood bank saline and phosphate buffered saline.

* * * * *